US010945686B2

(12) United States Patent
Halliburton et al.

(10) Patent No.: US 10,945,686 B2
(45) Date of Patent: Mar. 16, 2021

(54) SYSTEM FOR MEDICAL IMAGING

(71) Applicant: Motion Index Drives, Inc., Troy, MI (US)

(72) Inventors: Marc Halliburton, Troy, MI (US); Norbert Hofstetter, Hollenbach (DE); Sigmund Kumeth, Kastl (DE)

(73) Assignee: Motion Index Drives, Inc., Troy, MI (US)

( * ) Notice: Subject to any disclaimer, the term of this patent is extended or adjusted under 35 U.S.C. 154(b) by 0 days.

(21) Appl. No.: 16/796,399

(22) Filed: Feb. 20, 2020

(65) Prior Publication Data

US 2020/0187875 A1 Jun. 18, 2020

Related U.S. Application Data

(63) Continuation of application No. 16/213,313, filed on Dec. 7, 2018, now abandoned, which is a continuation of application No. 15/914,563, filed on Mar. 7, 2018, now abandoned, which is a continuation of application No. 15/526,549, filed as application No.
(Continued)

(51) Int. Cl.
*G01T 1/164* (2006.01)
*A61B 6/03* (2006.01)
*A61B 6/00* (2006.01)
*A61B 6/06* (2006.01)

(52) U.S. Cl.
CPC ............ *A61B 6/037* (2013.01); *A61B 6/4291* (2013.01); *A61B 6/44* (2013.01); *A61B 6/503* (2013.01); *G01T 1/1648* (2013.01); *A61B 6/06* (2013.01)

(58) Field of Classification Search
CPC .......... A61B 6/037; A61B 6/44; A61B 6/503; A61B 6/4291; A61B 6/06; A61B 6/03; G01T 1/1648; G01T 1/166
See application file for complete search history.

(56) References Cited

U.S. PATENT DOCUMENTS

| 5,648,659 | A | * | 7/1997 | Bourguignon | .......... | F02F 1/108 |
| | | | | | | 250/363.04 |
| 7,683,331 | B2 | * | 3/2010 | Chang | ................... | G01T 1/1648 |
| | | | | | | 250/363.04 |

(Continued)

OTHER PUBLICATIONS

Rozler et al., "Collimator Interchange system for adaptive cardiac imaging in C-SPECT", 2011, IEEE Trasnactions on Nuclear Science, vol. 58, No. pp. 2226-2333. (Year: 2011).*

*Primary Examiner* — Kiho Kim
(74) *Attorney, Agent, or Firm* — Quinn IP Law

(57) ABSTRACT

A patient imaging system for creating visual representations for analysis includes an imaging source and a patient support disposed proximate the imaging source configured to receive and support the patient. An imaging device is disposed adjacent to the patient support and incorporates at least one detector, one or more slats cooperating with the at least one detector and a collimator disposed between the one or more slats and patient support having a plurality of links adjustably positionable on the collimator. The plurality of links receive and support imaging plates that may be adjusted to provide a variety of image settings such that the imaging device and imaging source define a pre-determined imaging volume in an imaging region for the patient positioned in the imaging system.

20 Claims, 5 Drawing Sheets

Related U.S. Application Data

PCT/US2015/060910 on Nov. 14, 2014, now abandoned.

(60) Provisional application No. 62/080,239, filed on Nov. 14, 2014.

(56) References Cited

U.S. PATENT DOCUMENTS

| | | | | |
|---|---|---|---|---|
| 7,825,383 B2* | 11/2010 | Vija | ............... | A61B 6/037 |
| | | | | 250/363.05 |
| 2009/0022278 A1* | 1/2009 | Hugg | ............... | A61B 6/037 |
| | | | | 378/149 |
| 2011/0103544 A1* | 5/2011 | Hermony | ............... | A61B 6/037 |
| | | | | 378/19 |

* cited by examiner

SYSTEM FOR MEDICAL IMAGING

CROSS-REFERENCE TO RELATED APPLICATIONS

This application claims the benefit of U.S. application Ser. No. 16/213,313 filed Dec. 7, 2018, entitled "SYSTEM FOR MEDICAL IMAGING," which is a continuation of U.S. application Ser. No. 15/914,563 filed Mar. 7, 2018, entitled "SYSTEM FOR MEDICAL IMAGING," which is a continuation of U.S. application Ser. No. 15/526,549 filed May 12, 2017, entitled "SYSTEM FOR MEDICAL IMAGING," which is the National Stage of International Application No. PCT/US2015/060910 entitled "SYSTEM FOR MEDICAL IMAGING" filed Nov. 16, 2015, which claims priority to U.S. Provisional Patent Application No. 62/080,239 entitled "SYSTEM FOR MEDICAL IMAGING" filed on Nov. 14, 2014, all of which are incorporated by reference in their entirety.

TECHNICAL FIELD

The present disclosure relates to a medical imaging system to create a visual representation for analysis.

BACKGROUND

Imaging systems have revolutionized the medical industry. A practitioner's ability to identify, evaluate and propose treatment for a patient's medical condition is simplified with each advance in medical imaging technology. Medical imaging seeks to reveal internal structures hidden by the skin and bones, as well as to diagnose and treat disease. Medical imaging also establishes a database of normal anatomy and physiology to make it possible to identify abnormalities.

One such form of medical imaging is known as Single-Photon Emission Computerized Tomography or SPECT. SPECT is a nuclear medicine tomographic imaging technique using gamma rays to provide three-dimensional information. This information is typically presented as cross-sectional slices through the patient, but can be freely reformatted or manipulated as required.

The technique typically includes delivering a gamma-emitting radioisotope or radionuclide into the patient through injection into the bloodstream. On occasion, the radioisotope is a simple soluble dissolved ion, such as a radioisotope of gallium (III). A marker radioisotope is attached to a specific ligand to create a radio ligand, whose properties bind it to certain types of tissues, allowing the combination of ligand and radiopharmaceutical to be carried and bound to a place of interest in the body, where the ligand concentration is seen by a gamma-camera. The prevalence of coronary artery disease and the role SPECT imaging plays in its diagnosis continue to keep cardiac SPECT a critical modality in cardiac imaging.

SUMMARY

A patient imaging system for creating visual representations for analysis includes an imaging source and a patient support disposed proximate the imaging source configured to receive and support the patient. An imaging device is disposed adjacent to the patient support and incorporates at least one detector, one or more slats cooperating with the at least one detector and a collimator disposed between the one or more slats and patient support having a plurality of links adjustably positionable on the collimator. The plurality of links receive and support imaging plates that may be adjusted to provide a variety of image settings such that the imaging device and imaging source define a pre-determined imaging volume in an imaging region for the patient positioned in the imaging system.

In one embodiment of the disclosure, a collimator for use adjacent an imaging region of an imaging device includes a housing having a central portion, an inner concave shaped working area disposed adjacent the imaging region and an outer component storage area. The outer component storage area includes a plurality of arms extending radially outward from the central portion of the housing, the arms having an elongate body terminating at a rounded distal end. The outer component storage area may include five arm portions extending radially outward from the central portion of the housing.

At least one track is disposed on a periphery of the collimator housing. A plurality of links including one or more cam followers that movably engage the at least one track. The outer component storage area cooperates with the concave working area of the housing to form a closed loop arrangement increasing the linear distance of the track on the collimator housing. A preload wheel cooperates with the drive mechanism to translate the plurality of links about the track.

A drive mechanism adjustably positions the plurality of links about a travel path defined by the track on the housing. The drive mechanism includes a motor, a reducing gear driven by the motor and a cam rotatably connected to the reducing gear engaging the one or more cam followers of the plurality of links. The drive mechanism may also include at least one encoder cooperating with the motor configured to identify position of the plurality of links and a controller in electrical communication with the at least one encoder and motor to monitor and position of the plurality of links in the track on the periphery of the housing.

In one embodiment of the disclosure, the plurality of links receive and support one or more imaging plates that are moved by the plurality of links to position the imaging plates in the concave working area of the housing adjacent the imaging region of the imaging device. The track of the housing may be configured to receive 240 links provided in eight sets of thirty links. The plurality of links may be positioned on the track about 0.06 millimeters apart from the adjacent link.

In another embodiment of the disclosure, an imaging device for use in a patient imaging system includes at least one detector, one or more slats cooperating with the at least one detector and a collimator. The collimator includes a housing having a central portion configured to receive and support the at least one detector and one or more slats, an inner concave shaped working area defining an imaging region and an outer component storage area having a plurality of arms extending radially outward from the central portion of the housing. The outer storage compartment area arms include an elongate body terminating at a rounded distal end. The outer component storage area of the collimator housing may include five arm portions extending radially outward from the central portion of the housing.

At least one track disposed on about a periphery of the collimator housing. A plurality of links include one or more cam followers that movably engage the at least one track. A drive mechanism adjustably positions the plurality of links about a travel path defined by the track on the housing. The drive mechanism includes a motor, a reducing gear driven by the motor and a cam rotatably connected to the reducing gear engaging the one or more cam followers of the plurality of links. The drive mechanism further comprises at least one encoder cooperating with the motor configured to identify position of the plurality of links and a controller in electrical communication with the at least one encoder and motor to monitor and position of the plurality of links in the track on the periphery of the housing.

The plurality of links receive and support one or more imaging plates that are moved by the plurality of links to position the imaging plates in the concave working area of the housing adjacent the imaging region of the imaging device. In one embodiment of the disclosure, the imaging plates mounted to the plurality of links are configured in a first plate arrangement to acquire a scout scan using a relatively large, high sensitivity pre-determined imaging volume and are configured in a second plate arrangement to acquire an image of a patient. In another embodiment of the disclosure, the imaging plates mounted to the plurality of links are configured in a third plate arrangement for image attenuation correction to increase diagnostic accuracy of myocardial perfusion single-photon emission computerized tomography imaging and are configured in a fourth plate arrangement wherein a set of thin vertical lead plates are positioned to allow for computerized tomography or thermoacoustic computerized tomography imaging.

In another embodiment of the disclosure, a patient imaging system includes an imaging device having at least one detector and one or more slats cooperating with the at least one detector. A collimator is disposed proximate the imaging device including a housing having a central portion, an inner concave shaped working area and an outer component storage area having a plurality of arms extending radially outward from the central portion of the housing, the arms having an elongate body terminating at a rounded distal end. At least one track is disposed on a periphery of the housing. A plurality of links are configured to receive imaging plates, the links including one or more cam followers that movably engage the at least one track.

A patient support cooperates with the inner concave shaped working area of the collimator to receive and support the patient. An imaging source is disposed proximate the patient support and an imaging region is created between the imaging source and collimator of the imaging device defined proximate the concave working area of the collimator and patient support. The imaging plates on the plurality of links are configured in arrangements to provide a variety of image settings such that the imaging device and imaging source may define a pre-determined imaging volume in the imaging region for the patient positioned in the imaging system.

The collimator of the patient imaging system may include a drive mechanism to adjustably position the plurality of links about a travel path defined by the track on the housing. The drive mechanism includes a motor, a reducing gear driven by the motor and a cam rotatably connected to the reducing gear engaging the one or more cam followers of the plurality of links to position the imaging plates on the links in position adjacent the imaging region. The drive mechanism further comprises at least one encoder cooperating with the motor configured to identify position of the plurality of links and a controller in electrical communication with the at least one encoder and motor to monitor and position of the plurality of links in the track on the periphery of the housing.

The patient support may include an adjustably positionable seat movable to a variety of positions relative to the imaging device to allow precise placement of the patient in the imaging region. Alternatively, the imaging device may be adjustably positioned relative to the patient support to allow precise placement of the patient in the imaging region.

The imaging source and imaging device may utilize a combination of single photon emission computed tomography (SPECT) and computerized tomography (CT) to create imaging information for evaluation.

The above features and advantages, and other features and advantages of the disclosure, will be readily apparent from the following detailed description of the embodiment(s) and best mode(s) for carrying out the disclosure when taken in connection with the accompanying drawings and appended claims.

DETAILED DESCRIPTION

Figure 1:
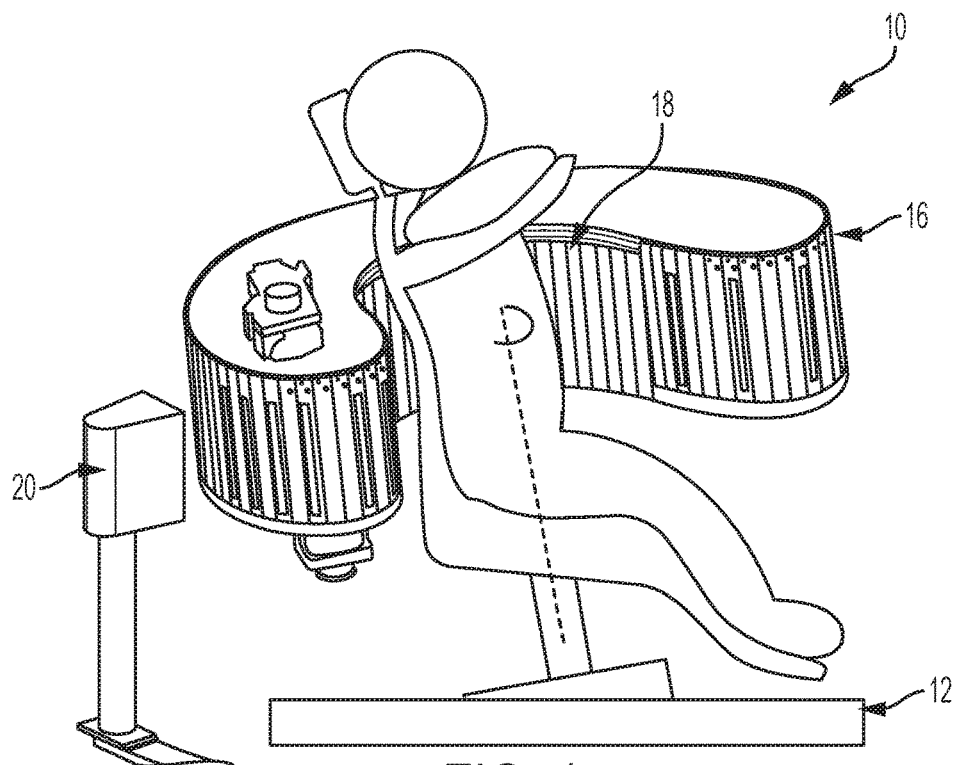
FIG. 1 is a perspective view of an imaging system in accordance with embodiments of this disclosure.

Reference will now be made in detail to several embodiments of the disclosure that are illustrated in accompanying drawings. Whenever possible, the same or similar reference numerals are used in the drawings and the description to refer to the same, or like parts or steps. The drawings are in simplified form and are not to precise scale. For purposes of convenience and clarity only, directional terms such as top, bottom, left, right, up, over, above, below, beneath, rear, and front, may be used with respect to the drawings. These and similar to directional terms are not to be construed to limit the scope of the disclosure: in any manner.

As required, detailed embodiments of the present invention are disclosed herein. However, it is to be understood that the disclosed embodiments are merely exemplary of the invention that may be embodied in various and alternative forms. The figures are not necessarily to scale. Some features may be exaggerated or minimized to show details of particular components. Therefore, specific structural and functional details disclosed herein are not to be interpreted as limiting, but merely as a representative basis for teaching one skilled in the art to variously employ the present invention.

Referring now to FIGS. 1-4, an exemplary system and method for creating visual representations or imaging of a patient for analysis by a medical professional is shown. It should be understood that many of the features described and shown in FIGS. 1-4, while known in the art, are illustrated herein for reference purposes as they relate to the inventive concept of the disclosure.

Referring to FIG. 1, the imaging system 10 includes a patient support 12 that may be affixed to a base or floor configured to receive and support a patient and an imaging device, generally referred to by numeral 16, disposed adjacent the patient support 12. Patient support 12 may be formed in a variety of configurations, such as a horizontal support such as a mobile table, hospital bed or the like. The patient support 12 may be adjustably positionable to allow positioning of a patient in up to three degrees of freedom to ensure the patient is properly positioned in the imaging system.

In one embodiment of the disclosure, patient support 12 may include a seat placed in a fixed position or may be adjustably positionable and movable to a variety of positions relative to the imaging device to allow easy entry and exit of patient from the imaging system or to allow precise placement of the patient adjacent the imaging device in an imaging region, generally represented by reference number 18. Alternatively, imaging device 16 may be adjustably positionable relative to the patient support 12 to accomplish a similar objective.

An imaging source 20 may be disposed proximate the patient support 12 and opposite the imaging device 16 so as to project energy toward the imaging device. In one embodiment of the disclosure, the imaging system utilizes single photon emission computed tomography (SPECT). In another embodiment of the disclosure, the imaging system utilizes computerized tomography (CT) imaging. In yet another embodiment of the disclosure, the imaging system may implement multiple imaging techniques simultaneously, such as SPECT and CT together to provide imaging information to the medical professional for evaluation. Exemplary imaging methods may also include X-ray radiography or fluoroscopy, positron emission tomography (PET), ultrasound, or magnetic resonance imaging.

Figure 2:
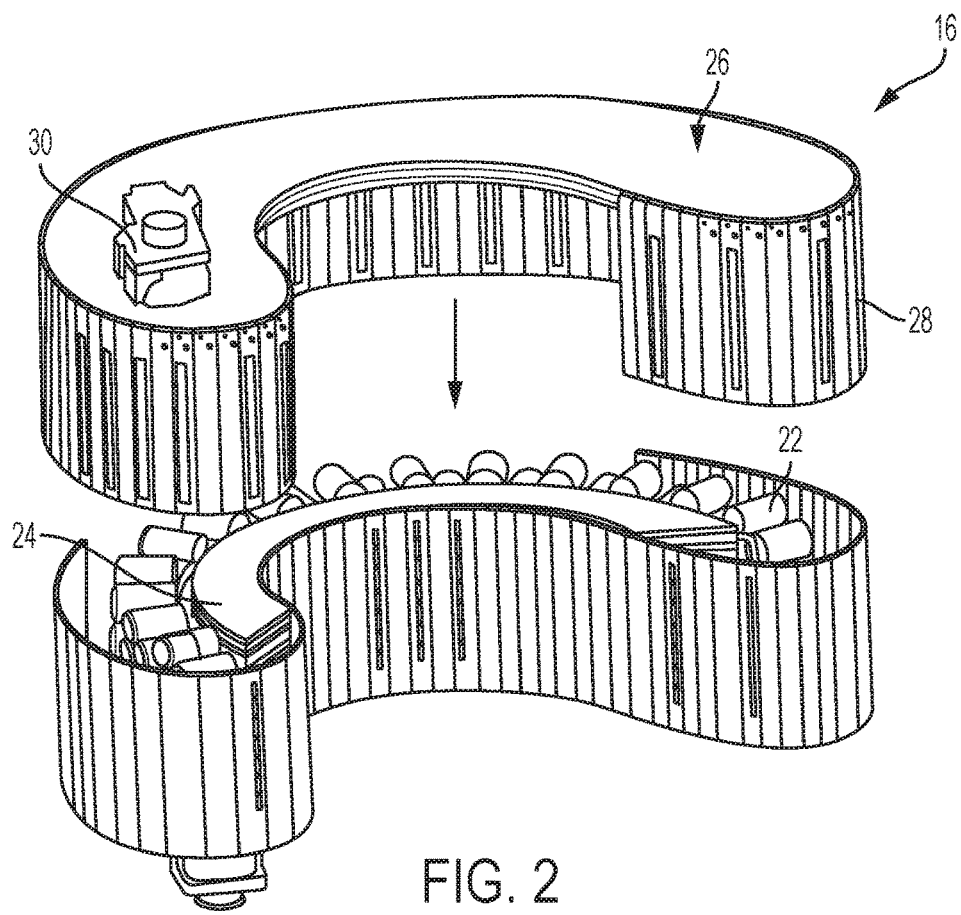
FIG. 2 is an exploded perspective view of an imaging device incorporating a collimator for use in the imaging system.
Figure 3:
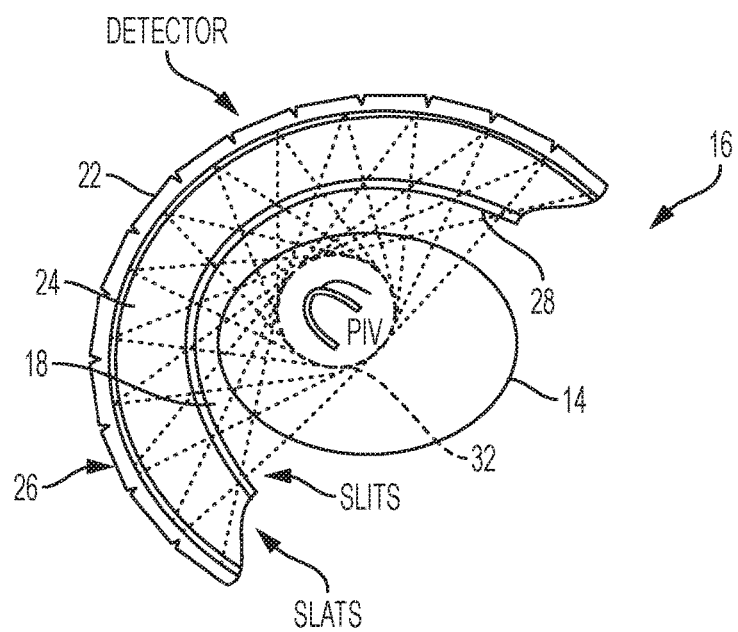
FIG. 3 is a schematic view of operation of the imaging device of the imaging system.
Figures 4A, 4B:
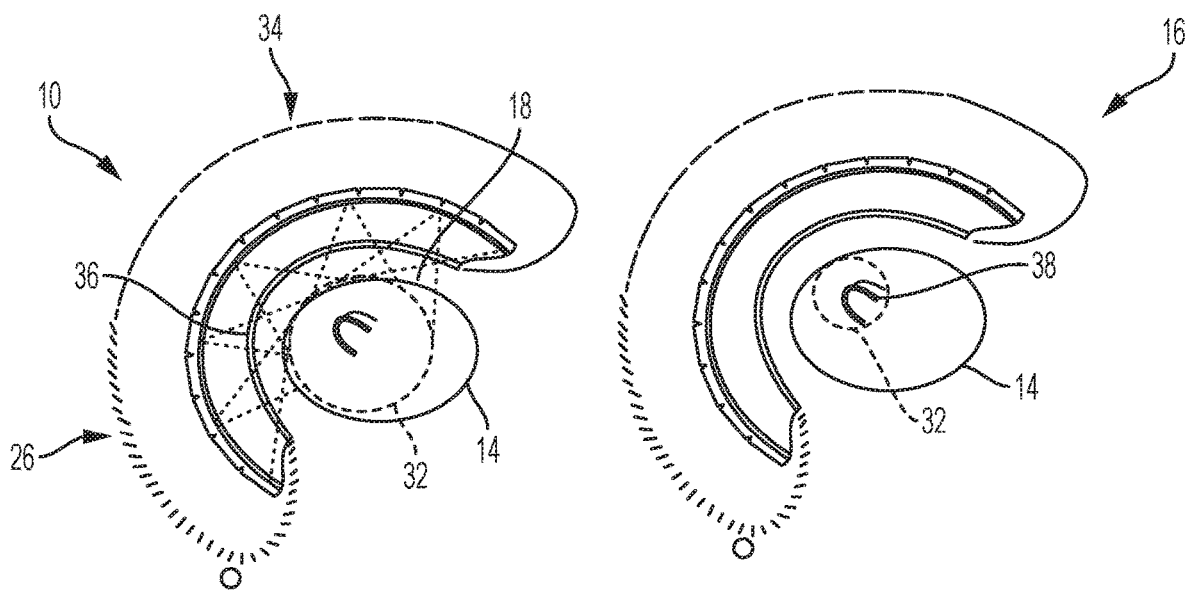
FIGS. 4(*a*)-(*f*) are schematic views representing exemplary alignment features of the imaging device.
Figure 4C:
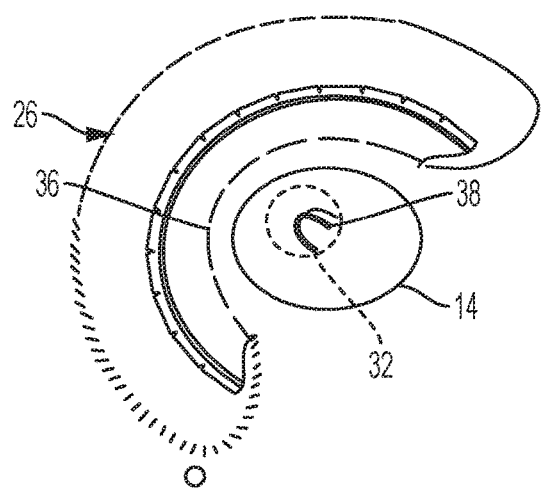
Figure 4D:
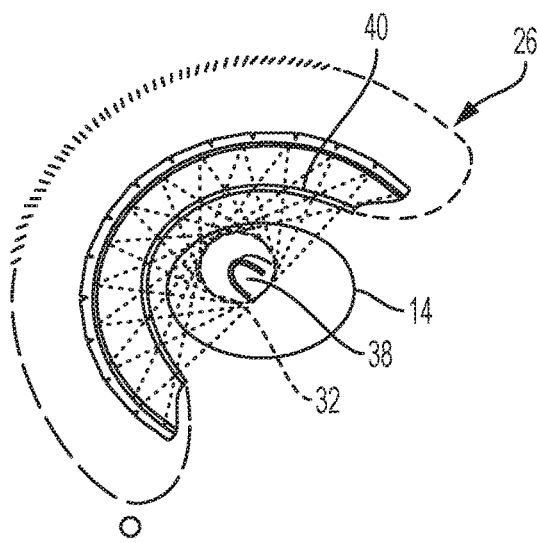
Figure 4E:
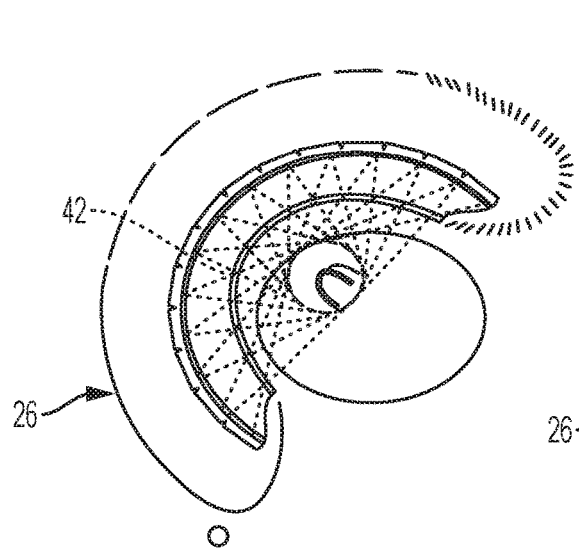
Figure 4F:
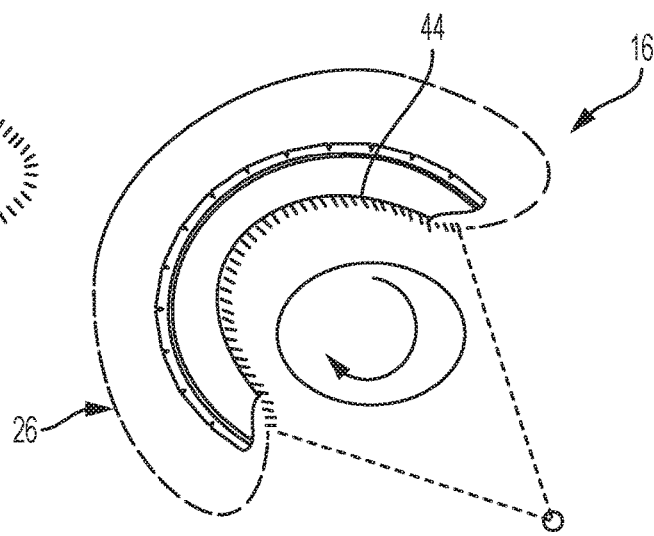
Figure 5:
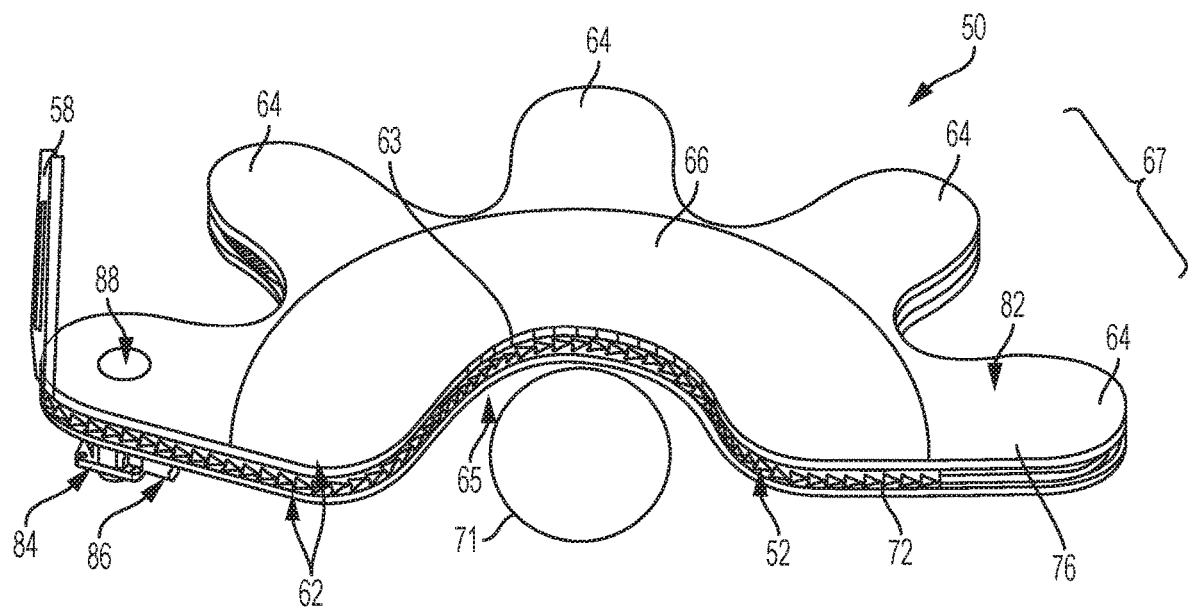
FIG. 5 is a perspective view of an upper surface of the imaging device for the imaging system in accordance with embodiments of the disclosure.

As is shown in FIG. 1, a patient 14 may be positioned on the patient support 12 within the imaging region 18 of the imaging device 16, such that the patient 14 is disposed between the imaging source 20 and the imaging device 16. Referring now to FIGS. 2 and 3, an imaging device 16 for use with embodiments of the disclosure is shown in greater detail. FIG. 2 illustrates an exemplary imaging device 16 incorporating at least one detector 22 cooperating with one or more slats 24. A collimator 26 may be disposed between the at least one detector 22, one or more slats 24 and the patient support 14 as shown in FIG. 1.

Collimator 26 generally includes a body-contouring design with a large area, high stopping-power, high packing-fraction detector 22 coupled with the slats 24 and plates 28 in the collimator 26 as best shown in FIG. 3. A plate-slat collimator for use with the imaging system of the disclosure may be designed around the concept of Pre-Determined Imaging Volume (PIV). As will be described in greater detail below, a motor 30 may be incorporated in the collimator to adjustably position the plurality of imaging plates of the plate segments 28 as the plates move along a path of travel defined by the geometry of the collimator 26.

Referring additionally to FIG. 4, patient 12 is positioned in the imaging region 18 of imaging system 10. It is understood that FIG. 4, as illustrated, is relevant for purposes of appreciating the inventive concept of the disclosure as set forth in FIGS. 5-8. The PIV is represented by a cylindrical field of view 32. In at least one embodiment of the disclosure shown in image (a) of FIG. 4, collimator 26 may be configured to include a plurality of plate arrangements, generally represented by reference numeral 34, to provide a variety of imaging features for the system 10.

For example, as shown in image (a) of FIG. 4, the imaging system may use a first plate arrangement 36 to acquire a scout scan using a relatively large, high sensitivity PIV 32.

In addition to localizing the target 38 of the patient, such as the heart or other relevant organ as shown in image (b) of FIG. 4, the data from the large scout PIV can be used to address any possible truncation artifacts resulting from the follow-up imaging with a small PIV. Based on the results of the scout scan, an appropriate PIV is selected from the available options of imaging plate segment arrangements from the imaging device 16 and the patient may be translated by the patient support to place the heart in the PIV 32 as shown in image (c) of FIG. 4, and the plate set may be changed to another plate arrangement such as the second plate arrangement 40 for imaging as shown in image (d) of FIG. 4.

A typical imaging PIV will tightly enclose the heart and allow around 12-16 simultaneous non-overlapping projections. The collimator exchange system also enables imaging for attenuation correction, while ensuring image co-registration through the use of a third plate arrangement 42 as shown in image (e) of FIG. 4. It is recognized that attenuation correction can increase diagnostic accuracy of myocardial perfusion SPECT imaging.

After the emission imaging, a set of thin vertical lead plates may replace the plates as a fourth plate arrangement 44 of the imaging device 16 as shown in image (f) of FIG. 4. In one embodiment of the disclosure, imaging plates may be vertical lead plates that block most of the photons emitted from the body, to avoid swamping the detector during imaging. The latter may be performed using an integrated line source, with patient rotated by the patient support for adequate sampling. In the present invention, the slats providing axial collimation will also be adjustable between high-resolution and high-sensitivity modes, without changing the PIV to allow for CT or thermoacoustic computerized tomography (TCT) imaging.

Referring now to FIGS. 5-8, a collimator 52 for use with an imaging device 50 for an imaging system is described in greater detail. The collimator of the imaging device may be formed as a precision link conveyor arrangement for use with a medical nuclear cardiac imaging system. The field of view of the imaging device may be optimized by selection and use of a desired number of imaging plate segments to provide transaxial collimation. It is understood that the imaging device for use in FIGS. 5-8 is shown in illustrative purposes in FIGS. 1-4. For example, an imaging device is disposed adjacent to the patient support and incorporates at least one detector, one or more slats cooperating with the at least one detector and a collimator disposed between the one or more slats and patient support having a plurality of links adjustably positionable on the collimator as shown in FIG. 2 will be used in connection with the collimator in FIGS. 5 and 6.

Referring now to FIGS. 5-8, an imaging device 50 in accordance with the disclosure is provided for use in the imaging system. The collimator 52 of imaging device 50 may include a precision link conveyor system that may be a transfer device capable of holding about eight sets of thirty links, or 240 links total, and be capable of receiving and transferring imaging plates secured to the links into position for use in the imaging process. In at least one embodiment of the disclosure, the precision link conveyor system of the collimator may adjust the links into position adjacent another link with a gap distance of about 0.06 millimeters.

Referring back to FIGS. 5 and 6, the collimator 52 of the imaging device includes a housing 62 having an inner concave shaped working area 63 disposed adjacent an imaging region 65, a central portion 66 and an outer storage compartment area 67 having a plurality of arms 64 extending radially outward from the central portion 66 of the housing 62. In one embodiment of the disclosure shown in FIGS. 5-6, a series of five arms each having an elongate body terminating at a rounded distal end extend radially outward from the central portion 66 of the housing 62. It is understood that outer storage compartment area 67 shown in FIG. 5 contemplates inclusion of all of the series of five arms the geometry and quantity of arms or extensions provided with on the outer storage compartment area may be adjusted based upon the imaging application.

The geometry of the imaging device may be affected by a number of factors, including shapes required for precise imaging, the number of links required for imaging, the number of plates or slats or limiting the overall size of the imaging device. In at least one embodiment of the disclosure, the housing 62 of collimator 52 of imaging device 50 may be configured to include an inner concave working area 63 in the housing 62 opposite the outer component storage area 67 to cooperate with the imaging region 65.

A track 76 is disposed about the outer periphery of the housing 62. The track 76 disposed on the outer periphery of the housing may be cut from a single piece of steel for use with custom links machined to adapt to handle the travel path within the imaging device. The outer component storage area cooperates with the concave working area of the housing to form a closed loop arrangement increasing the linear distance of the track on the collimator housing.

The number of arms or extensions are provided to maximize the amount of links and, thereby, imaging plates supported and used by the imaging system while decreasing the overall space requirements and area consumed by the imaging device, allowing for a more compact imaging system. For example, arms 64 may be configured to maximize the number of imaging plates for use with the system to obtain linear track distance and reduce the overall size of the unit.

The imaging plates may travel about the outer periphery of the housing around the arms or extension portions of the component storage area of the collimator housing to achieve an increased linear track distance. An equipment mounting area 68 may be provided on a top surface 70 of the housing 62, which may be used for the machine working area equipment requirements.

Figure 7:
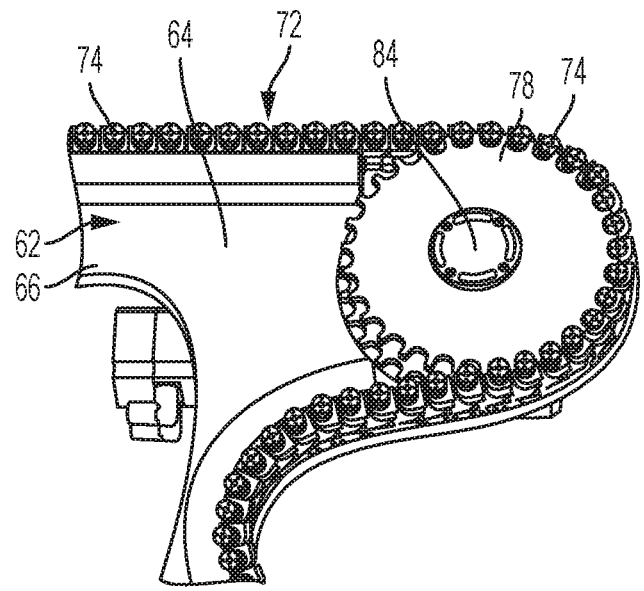
FIG. 7 is a perspective view of a portion of the drive system of the collimator of the imaging device for use with embodiments of the disclosure.

Referring now to FIG. 7, collimator 52 utilizes a plurality of links 72 formed from a variety of materials, including metals. In at least one of the embodiments of the disclosure, the links are formed from aluminum. Each link 72 may include one or more cam followers 74 connected thereto. In one embodiment of the disclosure, four cam followers are connected to each link. The cam followers 74 movably engage and translate through the track 76 to ensure accuracy of movement of the link in one or more degrees of freedom (DOF). Use of a track may ensure accuracy by eliminating backlash between the link followers and the track.

Imaging plate links 72 may be translated through the track by a drive mechanism. The drive mechanism includes a cam 78 rotatably connected to a reducing gear 74 driven by motor 86 disposed on a drive end 88 of the collimator housing 62. The cam 78 engages the cam followers 74 on the links 72. A preload wheel 80 on the non-drive end 82 of the collimator 52 cooperates with the drive mechanism to translate the plurality of links about the track.

In at least one of the embodiments of the disclosure, the drive mechanism of the collimator of the imaging device may also include an encoder cooperating with the shaft of the motor to identify the position used for the link exchange system operation. A controller is in electrical communication with the at least one encoder and motor. The controller may use a one-to-one correspondence between the encoder reading and the position of every moving element of the collimator to ensure that the controller monitors the positions of all imaging plate links due to the large number of the elements.

The plurality of links receive and support one or more imaging plates 56 that are moved by the plurality of links 72 to position the imaging plates in the inner concave working area 63 of the housing 62 adjacent the imaging region 65 of the imaging device 50. As shown generally in FIG. 5 and utilizing FIG. 4 in an illustrative nature, in one embodiment of the disclosure, the imaging plates 56 mounted to the plurality of links 72 are configured in a first plate arrangement to acquire a scout scan using a relatively large, high sensitivity pre-determined imaging volume, generally referenced by numeral 71, and are configured in a second plate arrangement to acquire an image of a patient.

In another embodiment of the disclosure, the imaging plates mounted to the plurality of links are configured in a third plate arrangement for image attenuation correction to increase diagnostic accuracy of myocardial perfusion singlephoton emission computerized tomography imaging. In yet another embodiment of the disclosure, the imaging plates are configured in a fourth plate arrangement wherein a set of thin vertical lead plates are positioned to allow for computerized tomography or thermoacoustic computerized tomography imaging.

Figure 6:
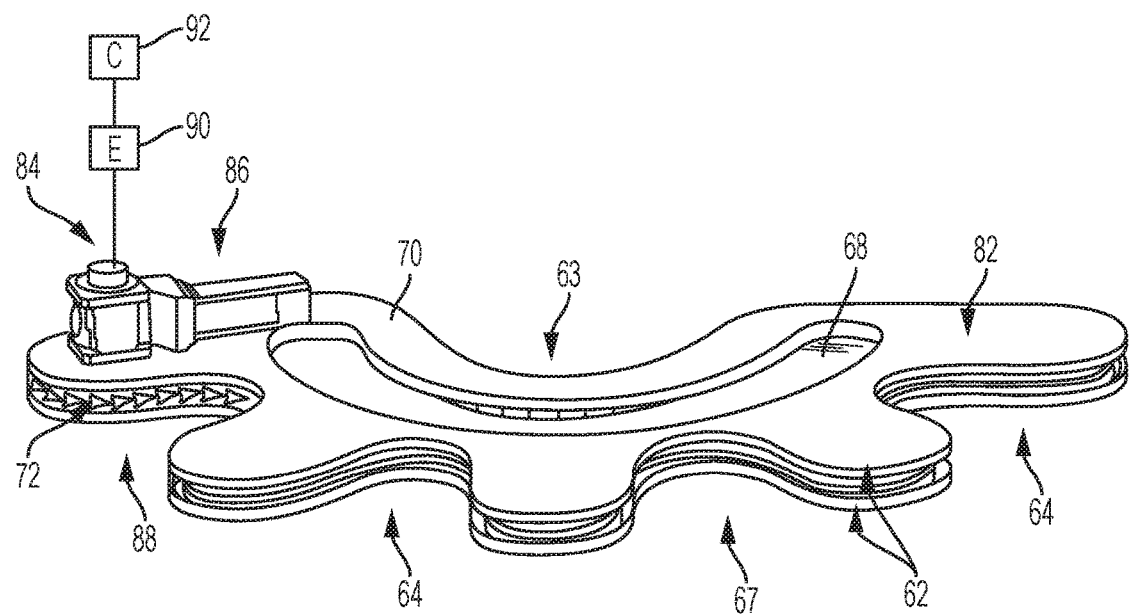
FIG. 6 is a perspective view of a lower surface of the imaging device of the imaging system.
Figure 8:
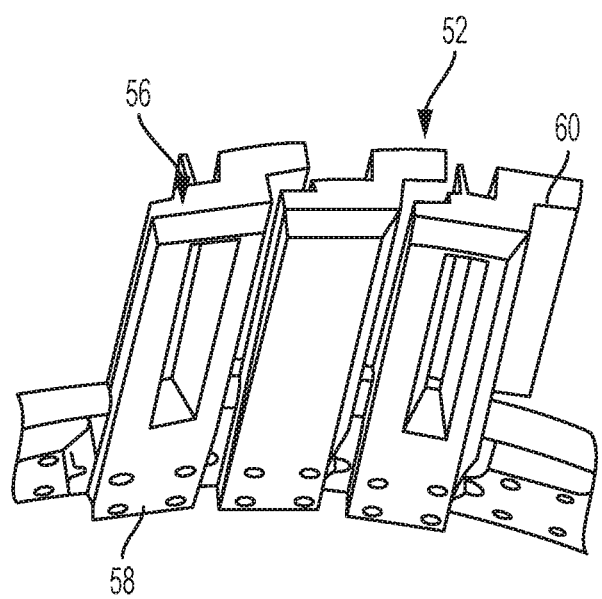
FIG. 8 is a perspective view a portion of the collimator illustrating plates for use with the imaging device.

Referring now to FIGS. 6 and 8, imaging plates 58 may be secured by a variety of fastening methods or materials to one or more of the plurality of links 72. Each plate 58 may be backed by a support structure 60 such as a steel plate to provide supplemental rigidity for the plate. The plates may utilize overlaps to prevent photons from the imaging process from leaking between the plates.

In one embodiment of the disclosure, collimator 52 may contain several sets of links 72, with each set dedicated to imaging a specific PIV. For example, collimator may include eight sets of imaging plates each associated with a link, with each set including a thirty imaging plates connected to thirty links. The imaging plates 58 on links 72 are exchanged precisely and rapidly, without disturbing the patient, to make imaging operations practical and accurate. As is best shown in FIG. 6, a collimator plate 56 is secured to link 72 and is moved about the outer periphery of the collimator housing 62 as link 72 translates through track 76. It is also contemplated that collimator 50 may at least partially wrap around the one or more slats and the at least one detector of the imaging device. The imaging plates may be grouped such that each group may be dedicated to an imaging task. In the exemplary embodiment, the plate segments are moved about the outer periphery of the housing to a position proximate the imaging region and patient support for imaging.

The detailed description and the drawings or figures are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims.

The invention claimed is:

1. A collimator for use adjacent an imaging region of an imaging device comprising:
  a housing having a central portion, an inner concave shaped working area disposed adjacent the imaging region and an outer component storage area having a plurality of arms extending radially outward from the central portion of the housing, the arms each having an elongate body terminating at a rounded distal end;

at least one track disposed on a periphery of the housing;

a plurality of links including one or more cam followers that movably engage the at least one track; and a drive mechanism adjustably positioning the plurality of links about a travel path defined by the track on the housing, the drive mechanism including a motor, a reducing gear driven by the motor and a cam rotatably connected to the reducing gear wherein the cam engages the one or more cam followers of the plurality of links, wherein the plurality of links receive and support one or more imaging plates that are moved by the plurality of links to position the imaging plates in the inner concave working area of the housing adjacent the imaging region of the imaging device.

2. The collimator of claim 1 wherein the drive mechanism further comprises at least one encoder cooperating with the motor configured to identify position of the plurality of links and a controller in electrical communication with the at least one encoder and motor to monitor the position of the plurality of links in the track on the periphery of the housing.

3. The collimator of claim 1 wherein the plurality of arms comprises five arm portions extending radially outward from the central portion of the housing.

4. The collimator of claim 3 wherein the outer component storage area cooperates with the concave working area of the housing to form a closed loop arrangement on the collimator housing.

5. The collimator of claim 4 wherein the track of the housing is configured to receive 240 links provided in eight sets of thirty links.

6. The collimator of claim 4 wherein each of the plurality of links are positioned on the track of about 0.06 millimeters apart from the adjacent link.

7. The collimator of claim 1 further comprising a preload wheel cooperating with the drive mechanism to translate the plurality of links about the track.

8. An imaging device for use in a patient imaging system comprising:

at least one detector;

one or more slats cooperating with the at least one detector;

a collimator including a housing having a central portion configured to receive and support the at least one detector and one or more slats, an inner concave shaped working area defining an imaging region and an outer component storage area having a plurality of arms extending radially outward from the central portion of the housing, each of the arms having an elongate body terminating at a rounded distal end and at least one track disposed on about a periphery of the collimator housing;

a plurality of links including one or more cam followers that movably engage the at least one track; and a drive mechanism adjustably positioning the plurality of links about a travel path defined by the track on the housing, the drive mechanism including a motor, a reducing gear driven by the motor and a cam rotatably connected to the reducing gear, wherein the cam engages the one or more cam followers of the plurality of links wherein the plurality of links receive and support one or more imaging plates that are moved by the plurality of links to position the imaging plates in the concave working area of the housing adjacent the imaging region of the imaging device.

9. The imaging device of claim 8 wherein the drive mechanism further comprises at least one encoder cooperating with the motor configured to identify position of the plurality of links and a controller in electrical communication with the at least one encoder and motor to monitor and position of the plurality of links in the track on the periphery of the housing.

10. The imaging device of claim 8 wherein the outer component storage area of the collimator housing further comprises five arm portions extending radially outward from the central portion of the housing.

11. The imaging device of claim 8 wherein the imaging plates mounted to the plurality of links are configured in a first plate arrangement to acquire a scout scan using a relatively large, high sensitivity pre-determined imaging volume.

12. The imaging device of claim 8 wherein the imaging plates mounted to the plurality of links are configured in a second plate arrangement to acquire an image of a patient.

13. The imaging device of claim 8 wherein the imaging plates mounted to the plurality of links are configured in a third plate arrangement for image attenuation correction to increase diagnostic accuracy of myocardial perfusion single-photon emission computerized tomography imaging.

14. The imaging device of claim 8 wherein the imaging plates mounted to the plurality of links are configured in a fourth plate arrangement wherein a set of thin vertical lead plates are positioned to allow for computerized tomography or thermoacoustic computerized tomography imaging.

15. A patient imaging system comprising:

an imaging device having at least one detector and one or more slats cooperating with the at least one detector;

a collimator disposed proximate the imaging device including a housing having a central portion, an inner concave shaped working area and an outer component storage area having a plurality of arms extending radially outward from the central portion of the housing, the arms having an elongate body terminating at a rounded distal end;

at least one track disposed on a periphery of the housing;

a plurality of links configured to receive imaging plates, the links including one or more cam followers that movably engage the at least one track;

a patient support cooperating with the inner concave shaped working area of the collimator to receive and support the patient;

an imaging source disposed proximate the patient support; and an imaging region between the imaging source and collimator of the imaging device defined proximate the concave working area of the collimator and patient support, wherein the imaging plates on the plurality of links are configured in arrangements to provide a variety of image settings such that the imaging device and imaging source may define a pre-determined imaging volume in the imaging region for the patient positioned in the imaging system.

16. The patient imaging system of claim 15 wherein the collimator further comprises a drive mechanism to adjustably position the plurality of links about a travel path defined by the track on the housing, the drive mechanism including a motor, a reducing gear driven by the motor and a cam rotatably connected to the reducing gear engaging the one or more cam followers of the plurality of links to position the imaging plates on the links in position adjacent the imaging region.

17. The imaging system of claim 15 wherein the drive mechanism further comprises at least one encoder cooperating with the motor configured to identify position of the plurality of links and a controller in electrical communication with the at least one encoder and motor to monitor and position of the plurality of links in the track on the periphery of the housing.

18. The patient imaging system of claim 15 wherein the patient support comprises an adjustably positionable seat movable to a variety of positions relative to the imaging device to allow precise placement of the patient in the imaging region.

19. The patient imaging system of claim 15 wherein the imaging device may be adjustably positioned relative to the patient support to allow precise placement of the patient in the imaging region.

20. The patient imaging system of claim 15 wherein the imaging source and imaging device utilize a combination of single photon emission computed tomography (SPECT) and computerized tomography (CT) to create imaging information for evaluation.

* * * * *